United States Patent
Ray

(10) Patent No.: US 9,222,891 B1
(45) Date of Patent: Dec. 29, 2015

(54) REFLECTOMETRY APPARATUS AND METHOD

(71) Applicant: John Howard Ray, Rock Hill, SC (US)

(72) Inventor: John Howard Ray, Rock Hill, SC (US)

(73) Assignee: Industrial Test Systems, Inc., Rock Hill, SC (US)

( * ) Notice: Subject to any disclaimer, the term of this patent is extended or adjusted under 35 U.S.C. 154(b) by 34 days.

(21) Appl. No.: 14/315,635

(22) Filed: Jun. 26, 2014

(51) Int. Cl.
*G01N 33/00* (2006.01)
*G01N 21/78* (2006.01)

(52) U.S. Cl.
CPC .............. *G01N 21/78* (2013.01); *G01N 2201/02* (2013.01); *G01N 2201/062* (2013.01); *G01N 2201/12* (2013.01)

(58) Field of Classification Search
CPC .................... G01N 21/78; G01N 2201/062
See application file for complete search history.

(56) References Cited

U.S. PATENT DOCUMENTS

| | | | |
|---|---|---|---|
| 5,498,547 | A | 3/1996 | Blake et al. |
| 5,656,502 | A | 8/1997 | MacKay et al. |
| 6,518,034 | B1 | 2/2003 | Phillips et al. |
| 6,541,269 | B1 | 4/2003 | Ramana et al. |
| 2008/0113398 | A1 | 5/2008 | Lin et al. |

OTHER PUBLICATIONS

MeterTech Inc., AccuTest Enzyme Inhibitor Testing Solution, www.metertech-inc.com, web pages (4), Jun. 19, 2009.
Industrial Test Systems, Inc., Pool Check i Reflectometer, photos (3), product launched at Nov. 2-4, 2011 trade show.

*Primary Examiner* — Sam P Siefke
(74) *Attorney, Agent, or Firm* — Timothy R. Kroboth

(57) ABSTRACT

The present invention is directed to a reflectometer-based apparatus and method for colorimetric analysis. Advantageously, the present invention includes use of a test strip provided with an aperture over which a translucent colorimetric, indicator-bearing matrix is affixed. In addition, the present invention beneficially includes a test strip holder that includes a test strip-holding channel provided with a white background.

20 Claims, 5 Drawing Sheets

REFLECTOMETRY APPARATUS AND METHOD

FIELD OF THE INVENTION

The present invention relates to reflectometer-based, colorimetric analysis.

BACKGROUND OF THE INVENTION

Disposable test strips provided with apertures have been used for analysis of biological fluids such as blood, urine and saliva, and for analyzing rinse water of medical equipment for the residual level of disinfecting or sanitizing agents such as chlorine. As illustrated by U.S. Pat. No. 6,541,269 to Ramana et al. and U.S. Pat. No. 5,498,547 to Blake et al., apertured test strips have also been used for pool, spa and tap water analysis.

In a typical analysis using a reflectometer, the reflectometer includes one or more light sources for emitting light at one or more selected wavelengths, an object being analyzed reflects a portion of the emitted light, and one or more reflectometer detectors or sensors is positioned to receive the reflected light. A processor analyzes the reflected light information and provides a test result.

When as illustrated by U.S. Pat. No. 6,518,034 to Phillips et al., an apertured test strip is used with a reflectometer, the test strip is inserted into the reflectometer so that the test strip aperture is in registration with a reflectometer light source. However, test strip insertion into a reflectometer allows potentially interfering or contaminating materials such as liquid drops and dirt and debris, to contaminate the reflectometer optics. In addition, positioning of a reacted test strip pad with respect to the reflectometer light source, may vary or the test strip pad may move during analysis, so as to produce inconsistent or inaccurate results.

A reflectometry apparatus illustrated by U.S. Patent Application No. 2008/0113398 to Lin et al., includes a foldable test strip holder that when open, provides a groove into which a test strip including an enzyme pad spaced apart from a color indicator pad, is placed. The test strip holder is provided with an aperture, and when closed, the opaque pads contact one another and the opaque, reacted color indicator pad may be viewed through the test strip holder aperture and the transparent support of the test strip. The exterior of the test strip holder and interior of the reflectometer provide a mating fit of the test strip holder within the reflectometer. However, that apparatus appears to have limited analytical applicability. For example, it requires an enzyme pad, addition of sample to the enzyme pad, and physical contact of the test strip pads with each other.

Despite improvements in colorimetric analysis, there continues to be a need for consistency of results and improved sensitivity.

SUMMARY OF THE INVENTION

The present invention is directed to a reflectometer-based apparatus and method for colorimetric analysis. The inventive apparatus includes a test strip holder, an apertured test strip and a reflectometer. The test strip includes a support provided with an aperture, and beneficially a translucent, colorimetric indicator-bearing, fluid permeable matrix disposed over the aperture. A face of the fluid permeable matrix is attached to the test strip support, and a face of the matrix opposite that face is advantageously an uncovered face to promote fluid flow through the matrix. The test strip may include one or more auxiliary reagent-bearing pads.

The exterior of the test strip holder and the interior of the reflectometer are advantageously shaped for mating fit of the test strip holder and the reflectometer. The test strip holder is provided with an aperture, and includes a longitudinal channel, and a portion of the channel beneficially provides a white background for analysis. The channel is advantageously configured to snugly receive at least a portion of the test strip and to facilitate appropriate positioning of the test strip aperture and test strip matrix over the white background.

When assembled, the test strip holder firmly holds the positioned test strip in place, and the white background of the channel is in registration with the test strip aperture and the test strip holder aperture. Beneficially, the test strip aperture faces away from the white background, and the opposite face of the test strip matrix is positioned over, and may be in contact with, the white background.

Also provided is an analytical method that utilizes the combination of a test strip provided with an aperture and that includes a colorimetric indicator-bearing, fluid-permeable, translucent matrix disposed over the aperture, and a test strip holder provided with an aperture and a test strip-receiving channel that includes a white background disposed to be in registration with the test strip holder aperture.

The inventive analytical method includes effecting liquid flow through the test strip aperture and the translucent matrix and thus into flowing contact with the indicator on the matrix for color development, withdrawing the test strip from contact with the liquid, positioning the test strip in the test strip holder channel so that the test strip aperture overlays the white background of the channel, positioning the test strip holder aperture over the test strip aperture and enclosing the channel to firmly hold the positioned test strip in place, inserting at least a portion of the test strip holder into a reflectometer whereby the relevant reflectometer light source is in registration with the test strip aperture, emitting a light beam of an appropriate wavelength through the test strip holder aperture and toward the test strip aperture whereby emitted light that passes through the translucent matrix, is reflected by the white background of the channel, detecting reflected light, and displaying an analytical result.

Additional advantages and beneficial features of the present invention are set forth in the drawing and detailed description, and in part will become apparent to those skilled in the art upon examination of the drawing and detailed description or may be learned by practice of the invention. As will be realized, this invention is capable of other and different embodiments than those described, and its several details are capable of modification in various respects, all without departing from the invention. Accordingly, the drawing and the detailed description are to be regarded as illustrative in nature, and not as restrictive.

BRIEF DESCRIPTION OF THE DRAWING

Reference now is made to the accompanying drawing which forms a part of the specification of the present invention.

DETAILED DESCRIPTION OF THE INVENTION

The present invention is useful for testing drinking water, pool and spa water, aquarium water, industrial and environmental water, and for other types of water testing. Medical applicability includes analysis of biological fluids and of rinse water of medical equipment such as dialysis equipment for the residual level of a disinfecting or sanitizing agent such as chlorine. Chlorine analysis also has application to food processing equipment. The present invention is also useful for analysis of organic liquids and of contaminating analytes in fluids such as brake fluid. For certain analytes, the present invention is especially useful for analysis of as little as 0.01 ppm (0.01 mg/L) of the analyte.

Figure 1:
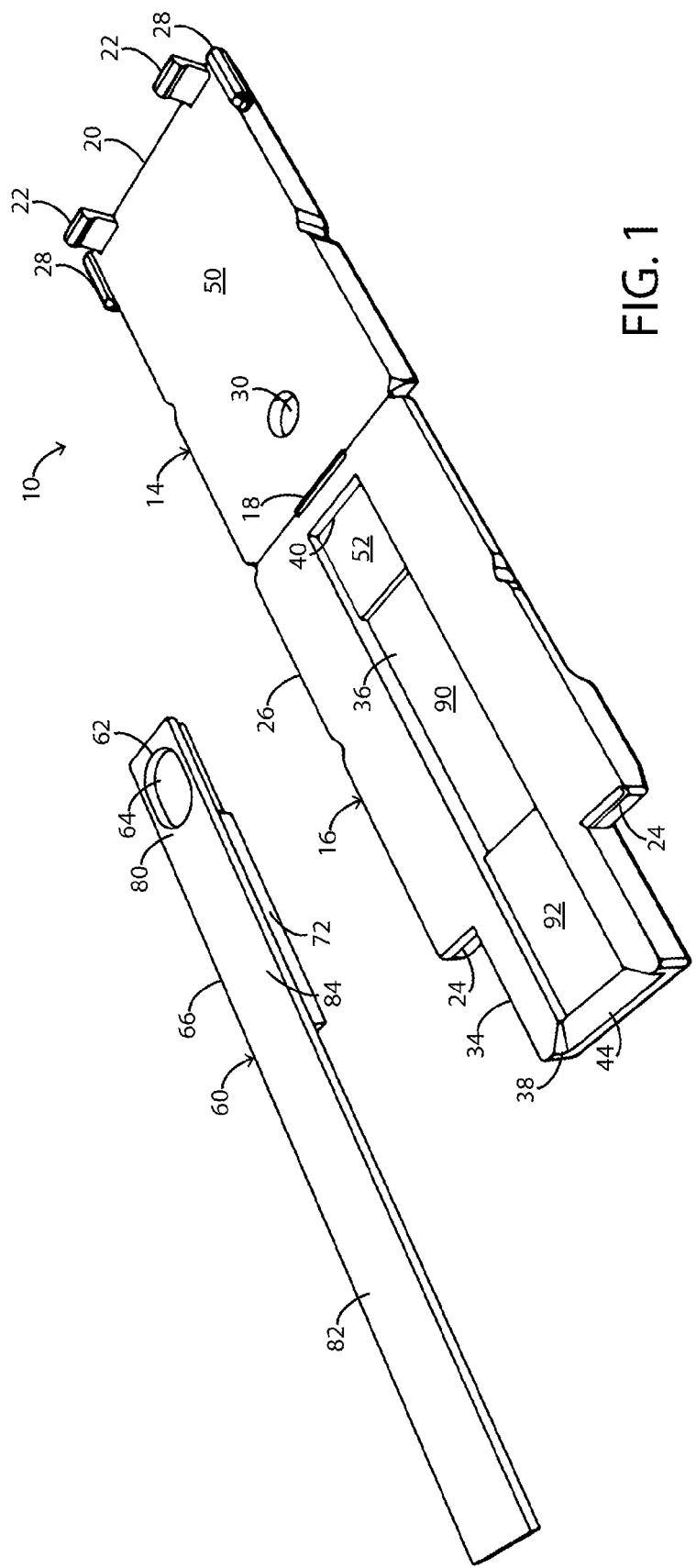
FIG. 1 is a perspective view of a preferred embodiment of a test strip and test strip holder in accordance with the present invention.
Figure 2:
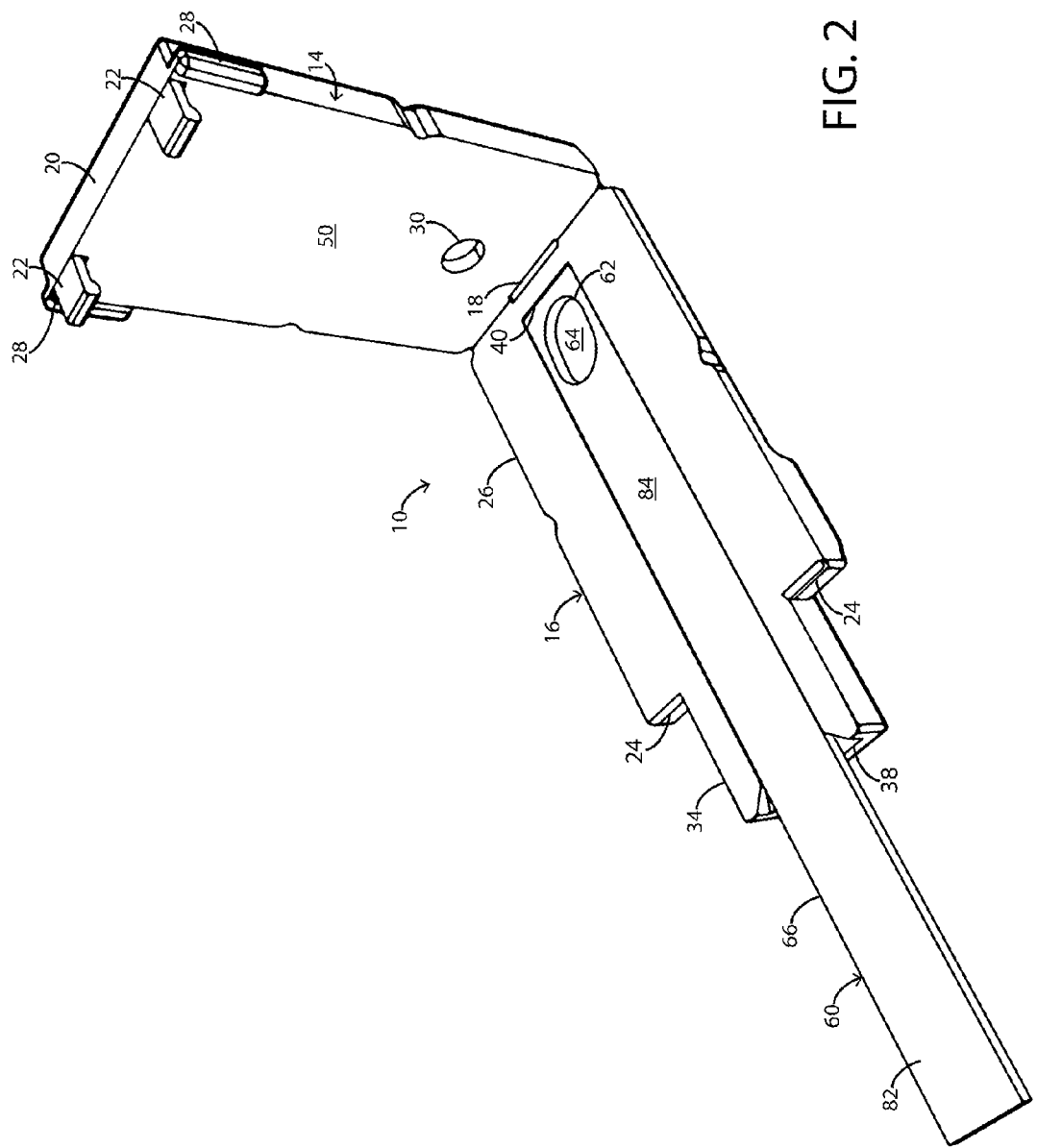
FIG. 2 is a perspective view of the test strip and test strip holder of FIG. 1, with the test strip positioned in the test strip holder, and the test strip holder partially closed.
Figure 3:
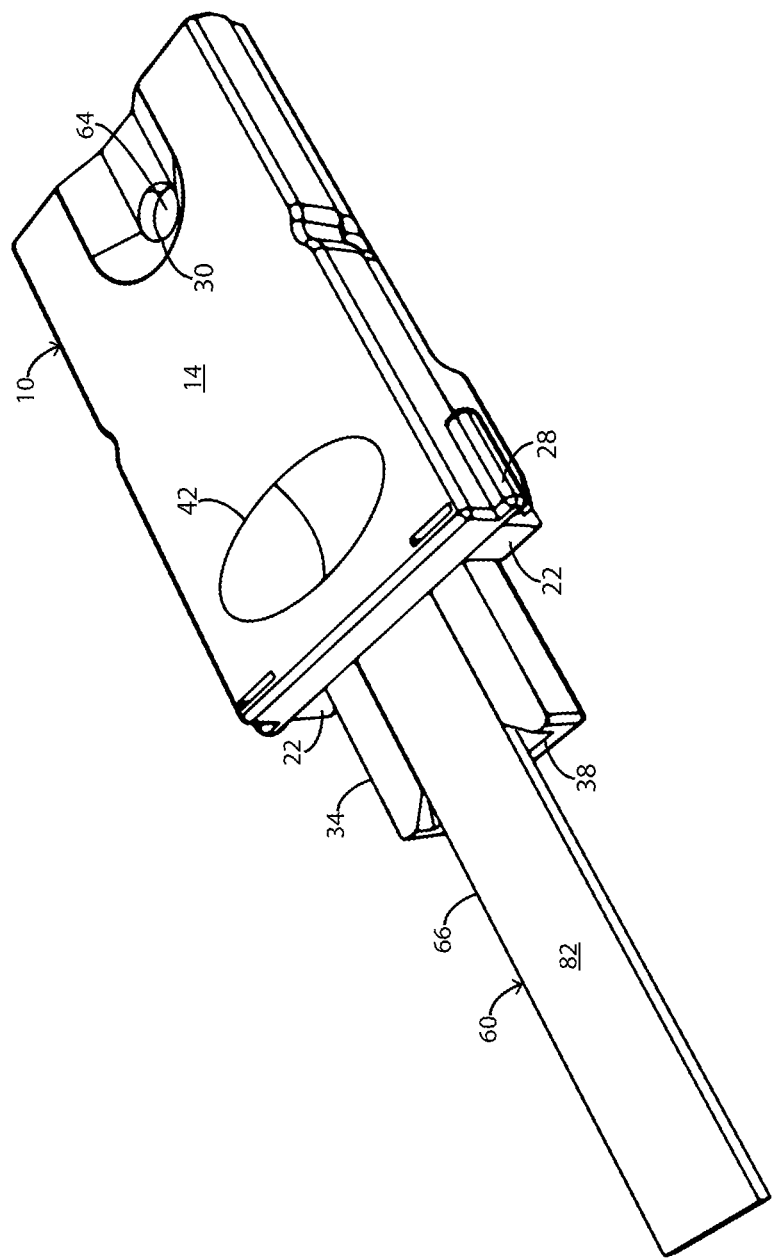
FIG. 3 is a perspective view of the test strip and test strip holder of FIG. 1, with the test strip positioned in the test strip holder, and the test strip holder closed.

The inventive apparatus includes a test strip holder, and a test strip provided with an aperture. Referring to FIGS. 1-3, an analytical apparatus in accordance with the present invention, beneficially includes a test strip holder 10 that includes a top or cover 14, and a bottom part 16 conveniently connected by a hinge 18. Conveniently extending from an end 20 of the cover opposite the hinge are a pair of spaced apart, generally L-shaped prongs 22 useful for engaging an end 24 of a main body 26 of bottom part 16 opposite the hinge. The cover and bottom part 16 conveniently fold together about the hinge, and prongs 22 advantageously snap the test strip holder closed. Grip tabs 28 assist disengagement of prongs 22 from main body end 24.

In an alternative embodiment, the test strip holder cover and bottom part are not hingedly connected, and the test strip holder may include two or more prongs or other useful engagement members, appropriately located for snapping the cover and bottom part 16 together. In yet another variation, instead of a top hinge such as top hinge 18, the cover and bottom part may be connected by one or more side hinges. Furthermore, a useful cover/bottom part engagement member may extend from the bottom part, rather than from the cover, as illustrated. Other variations will be apparent to one skilled in the art.

Test strip holder 10 is conveniently made of plastic, in which case hinge 18 is conveniently also plastic. As indicated by FIGS. 2 and 3, the hinge can be bent to close the test strip holder. Preferably, the test strip holder may be made of a black material to reduce interference by ambient light.

Cover 14 beneficially is provided with an aperture 30. Bottom part 16 of the test strip holder conveniently includes an extent 34 from main body 26, and is conveniently, as illustrated, generally planar except for a generally centrally located, longitudinal channel 36 beneficially dimensioned for snugly receiving a test strip. To this end, the width of the channel may preferably be substantially equal to the test strip width, as illustrated by FIG. 2. The channel depth may be conveniently stepped, as needed, as illustrated by FIG. 1.

Channel 36 conveniently extends from main body 26 to an end 38 of extent 34 opposite hinge 18. More specifically, channel 36 extends from a closed end 40 defined by main body 26, advantageously to an open, beveled end 44, which assists test strip removal. As an alternative to extent 34, bottom part 16 may be longer than illustrated, and the longitudinal channel may extend to, and terminate in, an open end defined by bottom part 16.

When the test strip holder is closed, a facing wall 50 of the cover cooperates with channel 36 to firmly hold a test strip positioned in the channel, in place during analysis, and the resulting tight fit around the test strip limits ambient light leaks. Facing wall 50 of the cover may, as illustrated, conveniently be generally planar, and advantageously when the test strip holder is closed, firmly contacts at least a portion of the test strip. An upper portion 52 of channel 36 is beneficially provided with a white background with which aperture 30 of the cover is disposed for registration when the test strip holder is closed. Consistent positioning of the test strip aperture and matrix over the white background is benefited. When the test strip holder is made of a black material, a white background may be provided by coating upper channel portion 52, or by any of other commercially suitable techniques. There are various shades of white, and any of these shades are contemplated for use in this invention.

With continued reference to FIGS. 1 to 3, the present invention advantageously includes a test strip 60 provided with an aperture 62, and a translucent, indicator-bearing, fluid-permeable matrix 64 disposed over the aperture. For purposes of this invention, the term "translucent matrix" as used herein, includes a transparent matrix and excludes an opaque matrix.

The apertured strip includes a support 66 conveniently made of an opaque thermoplastic such as PVC. If desired, the support may be made of a transparent material. A portion of matrix 64 surrounds the aperture and is attached to the support; and a face (not shown) of matrix 64 opposite the attached face is an uncovered face to promote fluid flow through the fluid permeable matrix.

Test strip aperture 62 may have a variety of shapes such as oval, as illustrated, and round. Advantageously, the aperture is limited in size to effectively direct fluid flow through a limited area of matrix 64. Conveniently, an oval aperture may be about 4 to 5 mm in width and about 4 to 6 mm in length.

Colorimetric indicators useful for free chlorine analysis include benzidine-type chromogens, diaminothiobenzophenone-type chromogens, and azine compounds such as syringaldazine and vanillinazine. Benzidine indicators are especially useful for evaluating free chlorine, and 3,3',5,5'-tetramethylbenzidine (TMB) is particularly preferred. TMB develops light blue to deep blue colors. To prevent leaching from the matrix in a water-based sample, the free base form is typically preferred.

Diaminothiobenzophenone indicators are especially useful for total chlorine analysis, and 4,4'-bis(dimethylamino) thiobenzophenone, also known as TMK, is particularly preferred. TMK develops green to deep blue-green colors, and is also useful for ozone analysis. Potassium iodide is typically used as a co-reagent for total chlorine analysis.

Other suitable colorimetric indicators are described in the prior art, with selection depending upon the analyte of interest. For example, colorimetric indicators useful for iron analysis include 2,4,6-tri(2-pyridyl)-1,3,5-triazine (TPTZ), and indicators useful for copper analysis include 5-(4-dimethylamino-benzylidene)rhodanine.

An apertured test strip in accordance with the present invention, may, as illustrated, include one or more auxiliary reagent pads, such as pad 72. For total chlorine analysis, an auxiliary potassium iodide pad is useful. As may be understood from FIG. 1, channel 36 may conveniently vary in depth as appropriate to accommodate differences in thickness of the test strip.

A useful test strip may be conveniently referred to as including an aperture end 80, a handle end 82, and between the aperture end and handle end, an intermediate or middle part 84. Beneficially, translucent matrix 64 may be thin, with a thickness of 0.2 to 0.5 mm being advantageous for permitting emitted light to pass through. Thus, typically, as illustrated in FIG. 1, an auxiliary test strip pad may be relatively thicker than translucent matrix 64. Furthermore, it is believed that a relatively thinner matrix pad, e.g., 0.25 mm vs. 0.4 mm thickness, may benefit sensitivity. However, matrix density is also an important consideration: a relatively less dense matrix can be relatively thicker, and depending on the density, the matrix can exceed 0.5 mm.

To accommodate the difference in thickness between an indicator-bearing matrix and an auxiliary pad, and describing channel 36 in such case with terms that correspond to a test strip positioned in the channel, a middle portion 90 of channel 36 may, as illustrated in FIG. 1, conveniently be relatively deeper than aperture (or upper) portion 52. When one or more auxiliary pads are disposed on a support surface opposite translucent matrix 64, facing wall 50 may, for example, have a recess that when the test strip holder is closed, accommodates auxiliary pad thickness.

Extent 34 from main body 26 conveniently provides support for a test strip and defines open end 44 of channel 36, and is, as illustrated, conveniently shorter than a test strip to assist test strip removal from the holder.

Figure 4:
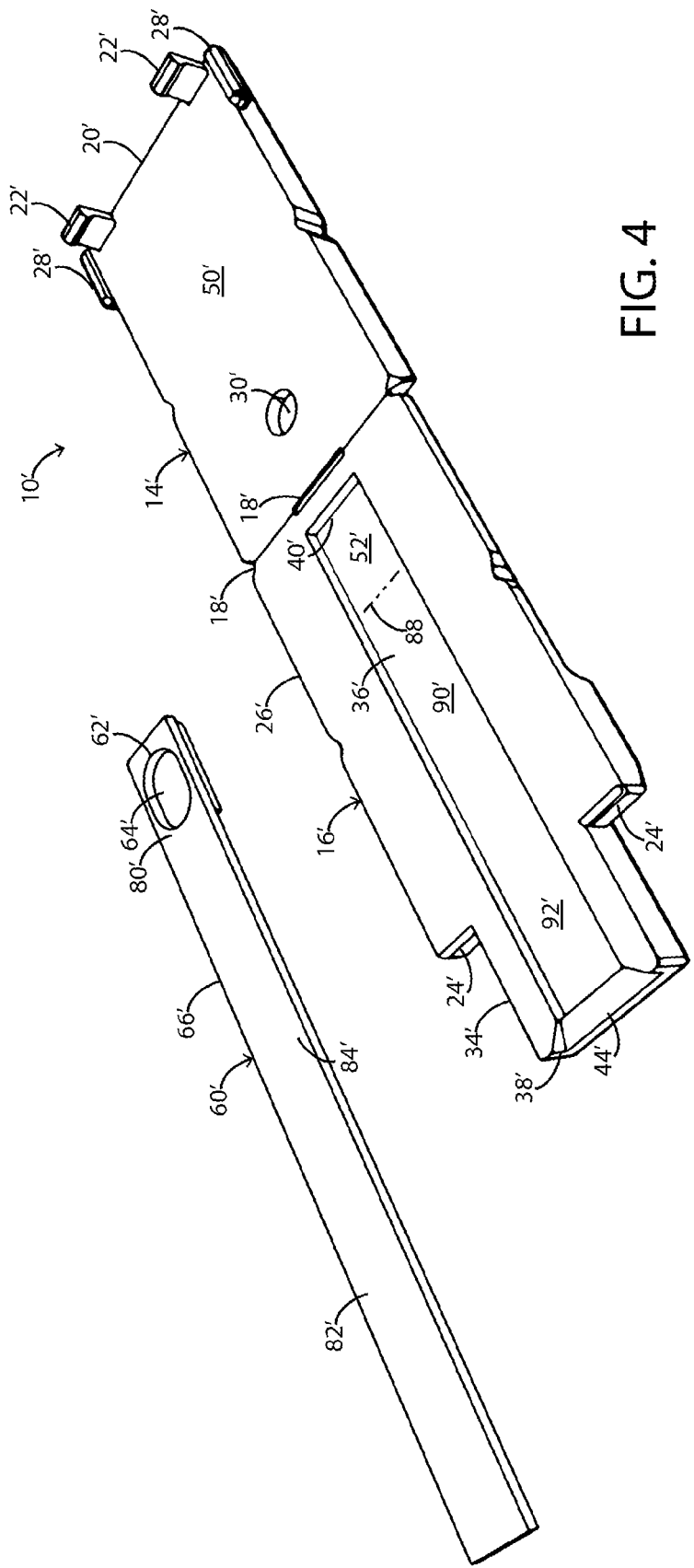
FIG. 4 is a perspective view of another preferred embodiment of a test strip holder.

Reference is now made to FIG. 2 and the description thereof in U.S. Pat. No. 6,549,269 to Ramana et al, which are hereby incorporated herein by reference, as illustrating a useful apertured test strip that lacks an auxiliary pad. A preferred test strip holder 10' for use with that type of test strip, is illustrated in FIG. 4, in which corresponding numbers have been used for parts corresponding to test strip holder 10 and of test strip 60. Unlike channel 36 of test strip holder 10, the depth of a handle portion 92' of longitudinal channel 36' of test strip holder 10' may be, as illustrated, substantially the same as the depth of a middle portion 90'. A phantom line 88 indicates separation of white background 52' of channel 36' from middle portion 90' of the channel.

In accordance with the invention, a facing wall of a cover of an inventive test strip holder beneficially exerts firm, generally uniform pressure on the aperture end of the test strip, and the face of the test strip matrix opposite the test strip aperture is pressured into contact with the white background of the channel. It is believed that consistent results are thereby benefited by providing a substantially constant path of emitted light through the test strip matrix to the white background, and a substantially constant path of reflected light through the matrix from the white background.

Figure 5:
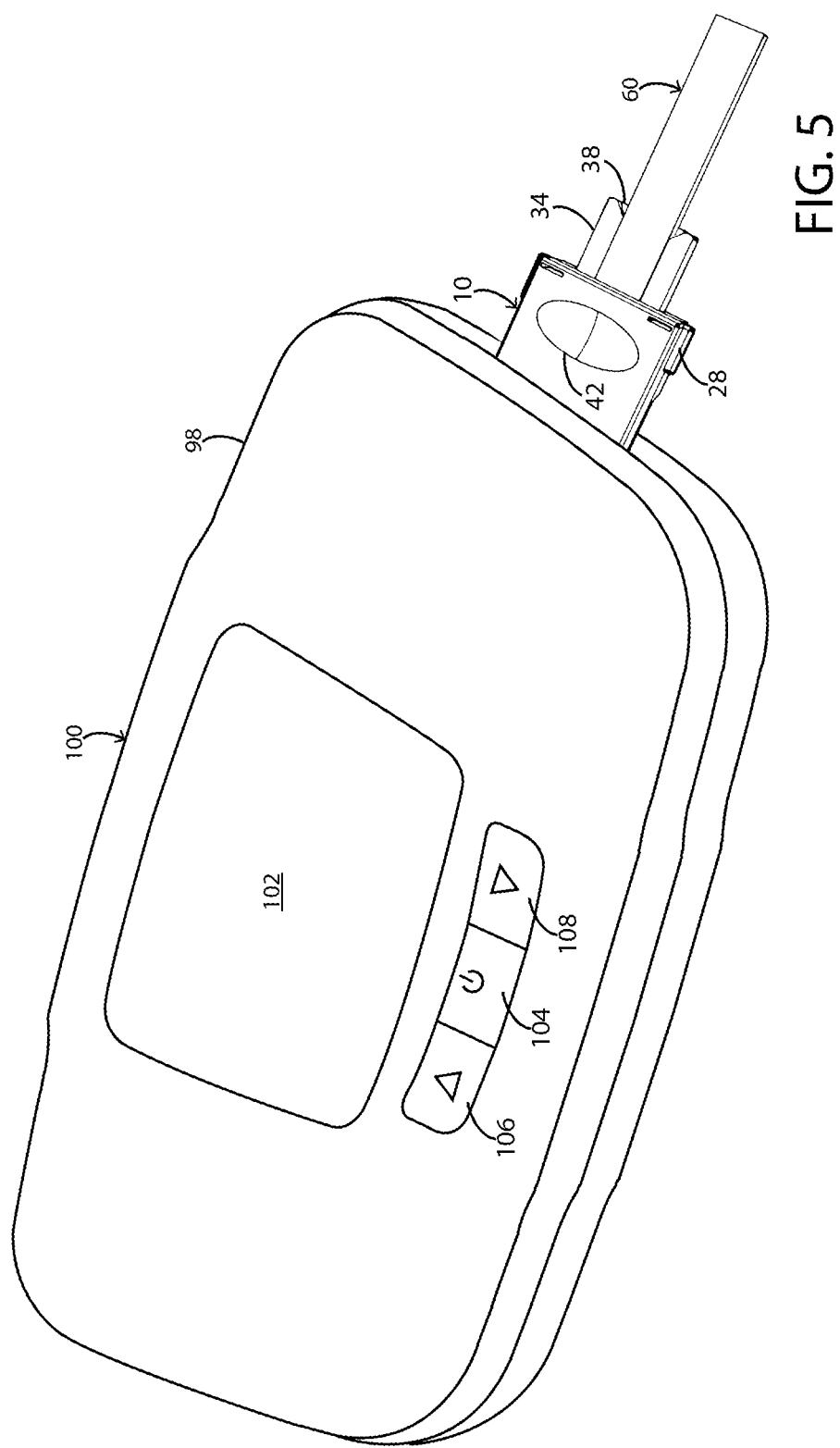
FIG. 5 is a perspective view of a reflectometer with the closed test strip holder of FIG. 3 partially disposed within the reflectometer.

With reference now to FIGS. 3 and 5, the interior (not shown) of the reflectometer and the exterior (shown in part in FIG. 3) of a test strip holder in accordance with the invention are beneficially shaped for receiving the test strip holder, and in particular to provide a mating fit of main body 26 of the test strip holder within the reflectometer, including appropriate positioning of aperture 64 with the reflectometer optics. A snug mating fit advantageously prevents interfering leaks of ambient light. Other shapes than that illustrated, may be used to provide a snug mating fit.

Advantageously, as illustrated, the test strip holder may be completely removed from the reflectometer to allow the test strip holder to be opened so as to provide access to the white background for cleaning. Removability is assisted by a concavity 42. When the test strip holder is closed, complete removability also allows a user to visually confirm the positioning of test strip holder aperture 30 over reacted matrix 64.

With continued reference to FIG. 5, a useful reflectometer 100 includes at least one light source for emitting light (not shown) and at least one reflected light detector or photoresistor (not shown) appropriately located for emitting and detecting light. When the test strip holder is inserted into the reflectometer, the light source, test strip holder aperture 30, test strip aperture 62, translucent matrix 64 of the test strip, and white background 52 of the test strip holder are in registration. Before placing a test strip in the test strip holder, the white background of the test strip holder may be beneficially used for blanking, that is, to obtain a baseline reading.

Light emitting diodes are useful light sources for reflectometry. The wavelength of the emitted light is selected based on the color development to be analyzed. For blue, blue-green and green color development, green light (about 495 to 570 nm) may be used. A wavelength of about 525 nm, may, for example, be convenient or advantageous, depending on the color development.

The reflectometer detector is in communication with a processor (not shown) that uses an algorithm to calculate the result from the data. Also in communication with the processor is a display 102, and control buttons 104, 106, 108 for operating the reflectometer.

For sake of brevity of this portion of the description of the invention, because the use of reflectometers for reading test strips is conventional, no further details are provided.

In accordance with the inventive method, the reagent-bearing pad or pads of an apertured test strip in accordance with the present invention, may be immersed in a liquid sample, and liquid flow through the test strip aperture and indicator-bearing matrix and into flowing contact with the colorimetric indicator on the matrix, is effected.

An apertured test strip may be moved within a liquid sample in a variety of useful ways, for instance, using back-and-forth or rotational motion, to cause flow through the indicator-bearing matrix. When a back-and-forth movement is used, a minimum number of back-and-forth strokes for, for example, about 20 seconds, may beneficially be about 20 to 22, with about 25 to 28 strokes generally being advantageous. Rigidity of the support assists effective movement of the indicator-bearing matrix. Advantageously, color development of the matrix within the area defined by the aperture is uniform. It is not necessary to immerse the matrix: the matrix may be contacted with flowing tap water.

The duration of contact of the indicator with the sample, is selected to ensure appropriate sensitivity. Within useful limits, a relatively greater contact time enables the test strip aperture to direct or channel relatively more fluid flow through a limited area and thus provides relatively more contact of the colorimetric indicator with an analyte of interest, and may thereby increase sensitivity. As illustrated by the Examples, about 10 to 30 seconds may be sufficient, with gentle, but rapid movement; however, it will be understood by one skilled in the art that more or less contact time may be appropriate depending on factors including the sensitivity of the test strip, the sensitivity desired, the colorimetric indicator and analyte.

The test strip is withdrawn from contact with the liquid sample, and may, as needed, be shaken lightly to remove excess liquid from the test strip. Traces of excess liquid on the white background of the channel may interfere with accurate results, and should be removed.

The test strip is positioned in the test strip holder channel so that the test strip aperture overlays the white background of the channel. Advantageously, the test strip aperture is positioned to face away from the white background, and, for consistency, the opposite face of the test strip matrix is positioned in contact with the white background. Contact with the white background may be assured by pressure of cover 14 on aperture end 80 of the test strip. Beneficially, matrix color is evaluated from the aperture side of the test strip. The color on the opposite face of the matrix may be non-uniform outside the area defined by test strip aperture.

The test strip holder is closed and inserted into the reflectometer. When the test strip holder is inserted, the reflectometer light source, test strip holder aperture, test strip aperture, and white background of test strip holder are in registration. After an appropriate wait time from withdrawal of the test strip from contact with the sample, a LED light source of the reflectometer emits a light beam of wavelength appropriate for the analysis, toward the strip aperture. Emitted light that passes through the translucent matrix, is reflected by the white background of the channel, and reflected light is detected by the reflectometer. The reflected light detected, includes emitted light reflected before reaching the white background. The reflectometer displays the result on display 102.

The wait time depends on factors including the duration of contact with the sample, the analyte and the sample temperature. A relatively longer wait time may be needed for a relatively cooler sample temperature.

Throughout this description which includes the Examples that follow, all parts and percentages are weight percent unless otherwise specified. The following examples illustrate application of the present invention to water-based samples, in testing for free chlorine, total chlorine and ozone.

Example 1

Total Chlorine 100 ml deionized water standards at 23 degrees C. are prepared containing 0 ppm, 0.05 ppm, 0.08 ppm, 0.13 ppm and 0.18 ppm total chlorine, as measured by the Hach DPD method.

An embodiment of the test strip of FIG. 1 is commercially available under the trademark Ultra Low Total Chlorine. This test strip provides visual color-matching for 0, 0.01, 0.02, 0.05, 0.1, 0.15 and 0.2 ppm total chlorine, and includes a thermoplastic support having a nominal width of 8 mm, length of 72 mm, and thickness of 0.01 inches (0.25 mm). Translucent matrix 64 has a nominal width of 8 mm, length of ½ inches, and thickness of 0.4 mm. Auxiliary pad 74 has a nominal width of 8 mm, one inch length, and thickness of 0.62 mm. The colorimetric indicator is TMK. The auxiliary pad is a potassium iodide-bearing pad.

A wavelength of 525 nm is used. White surface 52 of the test strip holder channel is used for blanking, that is, obtain a baseline reading, before a measurement.

For each liquid standard, the test strip described is moved to promote liquid flow through aperture 62 using 25 to 28 back-and-forth strokes for 20 seconds. The test strip is withdrawn from contact with the liquid, shaken lightly to remove excess liquid, and positioned in test strip holder channel 36 so that the test strip aperture overlays and faces away from white background 52. Test strip holder 10 is snapped closed to firmly hold the test strip in place, and partially inserted into reflectometer 100. Test strip aperture 62 is in registration with the reflectometer light source.

After a wait time of 20 seconds from withdrawing the test strip from contact with a liquid standard, a reflectometer LED emits a light beam toward the test strip aperture, reflected light is detected by a reflectometer sensor, the detected information is processed, and the reflectometer displays the percent reflectance. Each run is repeated. The results (White, % R) are set forth in Table 1.

Comparative Example 1

Total Chlorine

The procedure of Example 1 is followed except that black electrical tape is placed over the white background. Each run is repeated once. The results (Black, % R) are set forth in Table 1.

TABLE 1

| Total Chlorine (ppm) | White, % R | Black, % R |
|---|---|---|
| 0 | 66.7, 66.3 | 34.7, 34.9 |
| 0.05 | 44.3, 44.5 | 28.5, 25.6 |
| 0.08 | 40.6, 39.9 | 24.6, 24.8 |
| 0.13 | 38.6, 34.0 | 24.1, 20.5 |
| 0.19 | 36.6, 32.9 | 19.3, 20.7 |

These results demonstrate increased sensitivity resulting from use of a white background in the context of the present invention, up to about 0.1 ppm total chlorine.

Example 2

Total Chlorine 20 ml deionized water standards are prepared at room temperature containing the levels of total chlorine shown in Table 2. The levels of total chlorine are determined using the Hach DPD method.

An embodiment of the test strip of FIG. 4 is marketed under the trademark E-Z Check Sensitive TC. This test strip provides visual color-matching for 0, 0.1, 0.5 and 4 ppm total chlorine, and includes a PVC support having a nominal width of 8 mm, length of 72 mm, and thickness of 0.25 mm. The translucent matrix has a nominal width of 8 mm, length of ½ inches, and thickness of 0.34 mm, and is more dense than the Example 1 test strip. TMK and potassium iodide are used for color development.

Using E-Z Check Sensitive TC test strips, the procedure of Example 1 is followed, except that a 10 second contact time (with a reduced number of strokes) and 30 second wait time are used. Each run is repeated once. The results (White, % R) are shown in Table 2. Average values are in parenthesis.

Comparative Example 2

Total Chlorine

The procedure of Example 2 is followed, except that black electrical tape is placed over the white background. Each run is repeated once. The results (Black, % R) are shown in Table 2. Average values are in parenthesis.

TABLE 2

| Total Chlorine (ppm) | White, % R | Black, % R |
|---|---|---|
| 0 | 65.2, 65.1 (65.2) | 36.7, 33.0 (34.8) |
| 0.07 | 60.2, 55.2 (57.7) | 36.4, 32.0 (34.2) |
| 0.13 | 53.1, 57.8 (55.4) | 32.0, 31.5 (31.8) |
| 0.23 | 44.2, 48.2 (46.2) | 28.4, 29.4 (28.9) |
| 0.38 | 45.0, 42.0 (43.5) | 30.1, 25.6 (27.8) |
| 0.58 | 45.5, 40.9 (43.2) | 30.3, 30.0 (30.2) |
| 0.98 | 43.2, 42.7 (43.0) | 26.0, 26.2 (26.1) |
| 2.8 | 35.1, 35.2 (35.2) | 24.3, 22.0 (23.2) |

Lack of improved sensitivity for the 0.38, 0.58 and 0.98 ppm standards is consistent with the sensitivity levels of this test strip; otherwise, these results demonstrate increased sensitivity resulting from use of a white background in the context of the present invention, up to about 3 ppm total chlorine.

Example 3

Free Chlorine 50 ml deionized water standards are prepared at room temperature containing the levels of free chlorine shown in Table 3. The levels of free chlorine are determined using the Hach DPD method.

Another embodiment of the test strip of FIG. 4 is commercially available under the trademark SenSafe® Free Chlorine Water Check from Industrial Test Systems, Inc., Rock Hill, S.C. This test strip has a visual color-matching range of 0 to 4.0 and more than 6.0 for free chlorine, and includes a thermoplastic support having a nominal width of 8 mm, length of 72 mm, and thickness of 0.25 mm. The translucent matrix has a nominal width of 8 mm, length of ½ inches, and thickness of 0.4 mm. The colorimetric indicator is TMB.

Using SenSafe® Free Chlorine Water Check test strips, the procedure of Example 1 is followed, with each run being repeated once. The results (White, % R) are shown in Table 3.

Comparative Example 3

Free Chlorine

The procedure of Example 3 is followed, except that black electrical tape is place over the white background. Each run is repeated once. The results (Black, % R) are shown in Table 3.

TABLE 3

| Free Chlorine (ppm) | White, % R | Black, % R |
|---|---|---|
| 0 | 87.4, 89.0 | 45.6, 39.9 |
| 0.61 | 66.1, 66.5 | 38.6, 38.4 |
| 1.23 | 62.1, 64.0 | 34.1, 29.9* |
| 1.84 | 53.4, 58.3 | 23.7, 31.9 |
| 2.6 | 53.0, 49.0 | 23.7, 28.2 |
| 5.3 | 43.5, 47.7 | 24.0, 25.6 |

The run indicated with an asterisk, was repeated after wiping sample from the black background, to obtain a % Reflectance of 34.4, instead of 29.9.

These results demonstrate increased sensitivity resulting from use of a white background in the context of the present invention, up to about 1 ppm free chlorine. However, the wavelength of the emitted light was not optimized to the developed color; accordingly, a broader range of sensitivity may exist. Also, the developed color was very light, and wrinkling of the matrix after contact with some samples was observed: these factors are believed to have contributed to the inconsistency found with some repeat runs.

Example 4

Free Chlorine 50 ml deionized water standards are prepared at room temperature containing the levels of free chlorine shown in Table 4. The levels of free chlorine are determined using the Hach DPD method.

Using SenSafe® Free Chlorine Water Check test strips, the procedure of Example 3 is followed, except that a 30 second contact time (with an increased number of strokes) and no waiting time are used. Each run is repeated once. The results (White, % R) are shown in Table 4. Average values are in parenthesis.

Comparative Example 4

Free Chlorine

The procedure of Example 4 is followed, except that black electrical tape is place over the white background. Each run is repeated once. The results (Black, % R) are shown in Table 4. Average values are in parenthesis.

TABLE 4

| Free Chlorine (ppm) | White, % R | Black, % R |
|---|---|---|
| 0 | 84.4, 85.0 (84.7) | 36.2, 31.4 (33.8) |
| 0.03 | 85.4, 78.4 (81.9) | 33.1, 32.2 (32.7) |
| 0.08 | 76.6, 80.5 (78.6) | 33.0, 36.0 (34.5) |
| 0.17 | 75.2, 74.3 (74.8) | 44.8, 36.7 (40.8) |
| 0.38 | 72.4, 74.3 (73.4) | 28.1, 30.9 (29.5) |
| 0.54 | 71.3, 62.7 (67.0) | 28.2, 34.0 (31.1) |
| 0.78 | 57.2, 57.3 (57.3) | 37.2, 32.1 (34.7) |

These results further demonstrate increased sensitivity resulting from use of a white background in the context of the present invention, up to about 1 ppm free chlorine. It is believed that lack of optimization of the wavelength of the emitted light to the developed color, contributed to the lack of meaningful sensitivity between the results for the 0.17 and 0.38 ppm standards, using the white background. Again, the developed color was very light, and wrinkling of the matrix after contact with some samples was observed.

Example 5

Ozone 50 ml deionized water standards are prepared at room temperature containing the levels of ozone shown in Table 5. The ozone levels are determined using the Hach Indigo Method.

Another embodiment of the test strip of FIG. 4 is marketed under the trademark E-Z Check Ozone. This test strip provides visual color-matching for 0, 0.05, 0.1, 0.3 and more than 0.5 ppm ozone, and includes a thermoplastic support having a nominal width of 8 mm, length of 72 mm, and thickness of 0.25 mm. The translucent matrix has a nominal width of 8 mm, length of ½ inches, and thickness of 0.4 mm. The colorimetric indicator is TMK.

Using E-Z Check Ozone test strips, the procedure of Example 1 is followed. The results (White, % R) are shown in Table 5.

Comparative Example 5

Ozone

The procedure of Example 5 is followed, except that black electrical tape is placed over the white background. The results (Black, % R) are shown in Table 5.

TABLE 5

| Ozone (ppm) | White, % R | Black, % R |
|---|---|---|
| 0 | 68.6 | 26.9 |
| 0.01 | 57.4 | 35.4 |
| 0.05 | 48.0 | 28.1 |

TABLE 5-continued

| Ozone (ppm) | White, % R | Black, % R |
|---|---|---|
| 0.11 | 39.4 | 36.1 |
| 0.17 | 32.2 | 23.8 |
| 0.37 | 37.7 | 26.3 |
| 0.73 | 28.2 | 18.0 |
| 1.55 | 36.1 | 17.3 |

These results demonstrate increased sensitivity resulting from use of a white background in the context of the present invention, up to about 0.1 ppm ozone. Furthermore, sensitivity is found for an ozone level of 0.01 ppm, compared to color-matching. It is believed that ozone volatility may have affected data for some samples.

Various modifications and combinations have been described; other modifications will be readily apparent to one skilled in the art. The present invention may be carried out with other modifications and/or combinations without departing from the spirit or essential attributes thereof. Accordingly, reference should be made to the appended claims as indicating the scope of the invention.

The invention claimed is:

1. Analysis apparatus comprising
a test strip holder,
a test strip comprising a support provided with an aperture and attached to the test strip support, a colorimetric indicator-bearing matrix, and
a reflectometer;
wherein said test strip matrix is translucent and fluid-permeable, and comprises a first face in contact with said test strip support, and a portion of said first face is exposed by said aperture, and wherein said test strip matrix comprises an uncovered face opposite said first face;
wherein said test strip holder comprises a first part provided with an aperture and a second part comprising a test strip-receiving, longitudinal channel, and wherein a portion of said channel comprises a white background disposed for registration with the test strip holder aperture during analysis; and
wherein when assembled, said test strip is positioned in the channel, and said white background of said channel is in registration with the test strip aperture and the test strip holder aperture, and said uncovered face of the translucent test strip matrix is pressured into contact with said white background of said channel, and wherein said test strip aperture faces toward, and is in registration with, the test strip holder aperture and a reflectometer light source.

2. The analytical apparatus of claim 1, wherein said white background is an applied layer on said channel.

3. The analytical apparatus of claim 1, wherein said test strip holder is foldable, and said first part is hinged to said second part.

4. The analytical apparatus of claim 1, wherein the test strip holder channel terminates in an open end, and wherein when assembled, a portion of said test strip extends through said open end of said channel, and said open end is defined by said second part.

5. The analytical apparatus of claim 1, wherein when assembled, said first part cooperates with said second part to firmly hold a test strip positioned in said channel, in place.

6. The analytical apparatus of claim 1, wherein said test strip matrix has a thickness in the range of 0.25 to 0.5 mm.

7. The analytical apparatus of claim 1, wherein the test strip support has a thickness that is substantially the same as the depth of a handle end of said channel.

8. The analytical apparatus of claim 1, wherein the test strip support is opaque.

9. The analytical apparatus of claim 1, wherein the exterior of said test strip holder and the interior of said reflectometer are adapted for mating fit of said test strip holder and said reflectometer.

10. An analytical method that utilizes a test strip provided with an aperture and that comprises a colorimetric indicator-bearing, fluid-permeable, translucent matrix that comprises a first face a portion of which is disposed over the aperture and an uncovered face opposite said first face, and a test strip holder comprising a first part provided with an aperture and a second part comprising a test strip-receiving channel that includes a white background disposed for registration with the test strip holder aperture, and a reflectometer,
said analytical method comprising effecting liquid flow through the test strip aperture and through the uncovered face of the fluid-permeable, translucent matrix and thus into flowing contact with the indicator on the matrix for color development, thereafter withdrawing the test strip from contact with the liquid, positioning the test strip in the test strip holder channel so that said uncovered face of the translucent matrix faces the white background of the channel and said test strip aperture is disposed so as to face toward, and be in registration with, the test strip holder aperture, effecting registration of the test strip holder aperture with the test strip aperture and pressuring said uncovered face of the translucent matrix into contact with said white background, inserting at least a portion of the test strip holder into the reflectometer whereby the test strip aperture faces toward the reflectometer light source and the reflectometer light source is in registration with the test strip aperture, emitting a light beam of an appropriate wavelength through the test strip holder aperture and the test strip aperture whereby emitted light that passes through the translucent matrix, is reflected by the white background of the channel, detecting reflected light, and displaying an analytical result.

11. The analytical method of claim 10, further comprising using the white background of the channel for blanking prior to determining an analytical result.

12. The analytical method of claim 10, wherein the test strip-receiving channel terminates in an open end, and wherein when assembled, a portion of said test strip extends through said open end of said channel, and said open end is defined by said second part.

13. The analytical method of claim 10, wherein the test strip matrix has a thickness in the range of 0.25 to 0.5 mm.

14. The analytical method of claim 10, wherein the test strip comprises a support provided with said test strip aperture, and said first face of said translucent matrix is in contact with said test strip support.

15. The analytical method of claim 10, wherein the liquid flow is effected by movement within the liquid being analyzed.

16. The analytical method of claim 10, wherein the exterior of said test strip holder and the interior of said reflectometer are adapted for mating fit of said test strip holder and said reflectometer.

17. The analytical method of claim 10, wherein said test strip support is opaque.

18. The analytical method of claim 10, wherein said white background is an applied layer on said channel.

19. The analytical method of claim 10, wherein said test strip holder is made of a black material.

20. The analytical apparatus of claim 1, wherein said test strip holder is made of a black material.

\* \* \* \* \*